United States Patent [19]
Stenzler

[11] Patent Number: 5,937,854
[45] Date of Patent: Aug. 17, 1999

[54] VENTILATOR PRESSURE OPTIMIZATION METHOD AND APPARATUS

[75] Inventor: Alex Stenzler, Orange, Calif.

[73] Assignee: SensorMedics Corporation, Yorba Linda, Calif.

[21] Appl. No.: 09/003,717

[22] Filed: Jan. 6, 1998

[51] Int. Cl.⁶ .................................................. A61M 16/00
[52] U.S. Cl. ............................... 128/204.23; 128/204.18; 600/529
[58] Field of Search .......................... 128/204.23, 204.18, 128/204.21, 204.22, 204.26, 205.24, 898, 200.24; 600/529–534

[56] References Cited

U.S. PATENT DOCUMENTS

| | | | |
|---|---|---|---|
| 5,353,788 | 10/1994 | Miles | 128/204.23 |
| 5,542,415 | 8/1996 | Brody | 128/204.23 |
| 5,575,283 | 11/1996 | Sjoestrand | 128/204.23 |
| 5,738,090 | 4/1998 | Lachmann et al. | 128/204.23 |

OTHER PUBLICATIONS

Eric L. DeWeese, Thomas Y. Sullivan, and Pao L. Yu, "Ventilatory response to high–frequency airway oscillation in humans," J. Appl. Physiol. 58(4):1099–1106, 1985.

Herman L. Watson, Darell A. Poole, and Marvin A. Sackner, "Accuracy of respiratory inductive plethysmographic cross–sectional areas," J. Appl. Physiol. 65(1):306–308, 1988.

Päivi Valta, M.D.; Jukka Takala, M.D., Ph.D.; Robert Foster, Sc.D.; Charles Weissman, M.D.; and John M. Kinney, M.D.; "Evaluation of Respiratory Inductive Plethysmography in the Measurement of Breathing Pattern and PEEP–Induced Changes in Lung Volume," Chest, 102(1):234–238, Jul. 1992.

Primary Examiner—John G. Weiss
Assistant Examiner—Charles W. Anderson
Attorney, Agent, or Firm—Lyon & Lyon LLP

[57] ABSTRACT

A method and apparatus for ventilator pressure and optimization administers fixed stepwise pressure changes to the lungs of a patient and measures the lung volume change resulting from each pressure change. Critical opening pressure, critical closing pressure, and overdistention pressure are determined by changes in lung volume corresponding to the fixed stepwise pressure changes.

13 Claims, 3 Drawing Sheets

VENTILATOR PRESSURE OPTIMIZATION METHOD AND APPARATUS

BACKGROUND OF THE INVENTION

The invention relates generally to measurement of lung volume at different inspiration and expiration pressures during artificial ventilation of humans or other mammals. More particularly, this invention relates to the utilization of those measurements to determine the optimum range of pressures for artificial ventilation.

Frequently, a sick patient must be assisted in breathing by a ventilator. This patient may be human, or a nonhuman mammal. During conventional mechanical ventilation (CMV), the lung is inflated with a distending pressure called positive end expiratory pressure (PEEP). During high frequency ventilation (HFV), the lung is inflated with a distending pressure called mean airway pressure (Paw).

In a diseased lung, some air sacs may collapse, preventing gas from entering or leaving and thereby preventing gas exchange through those air sacs. Because a fewer number of air sacs are available for gas exchange, the patient must be ventilated with a higher concentration of oxygen than normal to enable his or her remaining open air sacs to provide adequate blood oxygenation. While a high oxygen concentration is required to provide adequate blood oxygenation and keep the patient alive, it is also toxic.

During inflation of the lung with increasing PEEP or Paw, the pressure increases and the collapsed air sacs of the lung begin to open, allowing them to once again take part in gas exchange. The pressure at which the air sacs begin to open is called the critical opening pressure. Air sacs opened because of ventilator inflation pressure are said to be recruited. As the number of recruited air sacs increases, the amount of oxygen that diffuses into the arterial blood also increases. This is reflected as an increase in blood oxygen saturation level, as may be non-invasively measured by pulse oximetry or directly with an arterial blood gas measurement. The increase in oxygen in the blood enables the caregiver to lower the inspired oxygen concentration toward less toxic levels. For these reasons, it is generally beneficial to recruit as many air sacs as possible in a patient undergoing ventilation.

When an increase in ventilator pressure fails to improve the oxygen saturation level of the blood, the lung is considered to be stable. If additional pressure is added to a stable lung, the patient runs the risk of experiencing overinflation. Overinflation significantly increases the chances for lesions to form in the lung tissue. Such lesions can allow air to leak into the space between the lungs and the chest wall, and can be lethal.

If the lung has been pressurized to the point of overinflation during recruitment, pressure cannot simply be reduced incrementally. Due to the elasticity of the lungs, which causes a nonlinear pressure/volume relationship which is different for inhalation than exhalation, a pressure decrease does not lead to a significant lung volume decrease until decruitment of air sacs begins. This pressure at which the air sacs begin to derecruit is called the critical closing pressure. A simple pressure decrease therefore leaves the lung in the same dangerous overinflated condition. Consequently, to prevent overinflation in a given patient, ventilator pressures may be significantly reduced to a lower level to find the safest pressure with the air sacs recruited. However, when the pressure is significantly reduced, the patient's blood oxygen can fall to dangerously low levels due to derecruitment of air sacs. As can be seen, this trial and error method is risky for the ventilated patient.

Underinflation of the lung creates another set of physical problems. If the lung is underinflated, diseased lung tissue may be derecruited, causing a condition called atelectasis. That is, diseased air sacs that took part in gas exchange when the lung was properly inflated (i.e., air sacs that had been recruited) will no longer do so if the inflation pressure is too low. Those air sacs will close again, and no gas exchange will take place through them, inhibiting the patient's ability to absorb oxygen and jettison carbon dioxide. Underinflation thereby causes atelectasis, which may be a life-threatening condition. Finally, underinflation can result in the release of chemicals in the lung tissue that induce biochemical lung injury.

Given the dangers of overinflation and underflation, the pressure output of a ventilator must be high enough to prevent underflation, and low enough to prevent overinflation. In the case of HFV, the mean airway pressure (Paw) must fall in this range between underinflation and overinflation. In the case of CMV, PEEP must fall in this range.

Currently, frequent chest X-rays are used clinically to determine an appropriate inflation pressure and to detect over- or under-inflation of the lungs. These frequent X-rays are undesirable for several reasons. First, they are clinically impractical when making frequent adjustments in ventilator settings. Second, they expose the patient to a significant cumulative dose of X-ray radiation during the course of ventilation. Third, accurately determining lung volume from a chest X-ray is difficult at best. Finally, frequent X-rays are costly to perform.

SUMMARY OF THE INVENTION

The present invention provides a ventilation pressure optimizer method and apparatus designed to satisfy the aforementioned needs. Accordingly, the present invention relates to method and apparatus for ventilation pressure optimization, which includes the steps of: (1) increasing the pressure to the lungs in substantially equal stepwise increments; (2) measuring the lung volume at each of said stepwise pressure increments; (3) calculating the lung volume change resulting from the present stepwise pressure increment; and (4) stopping when said lung volume change is greater than 120% than the lung volume change resulting from the previous stepwise pressure increment.

In the preferred embodiment of the apparatus, a computing device controls the increasing stepwise pressure increments to the patient and measures the pressure and volume at each increment, automatically stopping when the critical opening pressure or the critical closing pressure has been found.

DETAILED DESCRIPTION OF THE PREFERRED EMBODIMENTS

When a patient is on ventilation, either CMV or HFV, one of the caregiver's objectives is to recruit as many of the lung's air sacs as possible. Another objective is to avoid the potentially life-threatening problems of overinflation or underinflation. In order to meet both of these objectives, it is necessary to determine the critical opening pressure and critical closing pressure of the lung.

Figure 1:
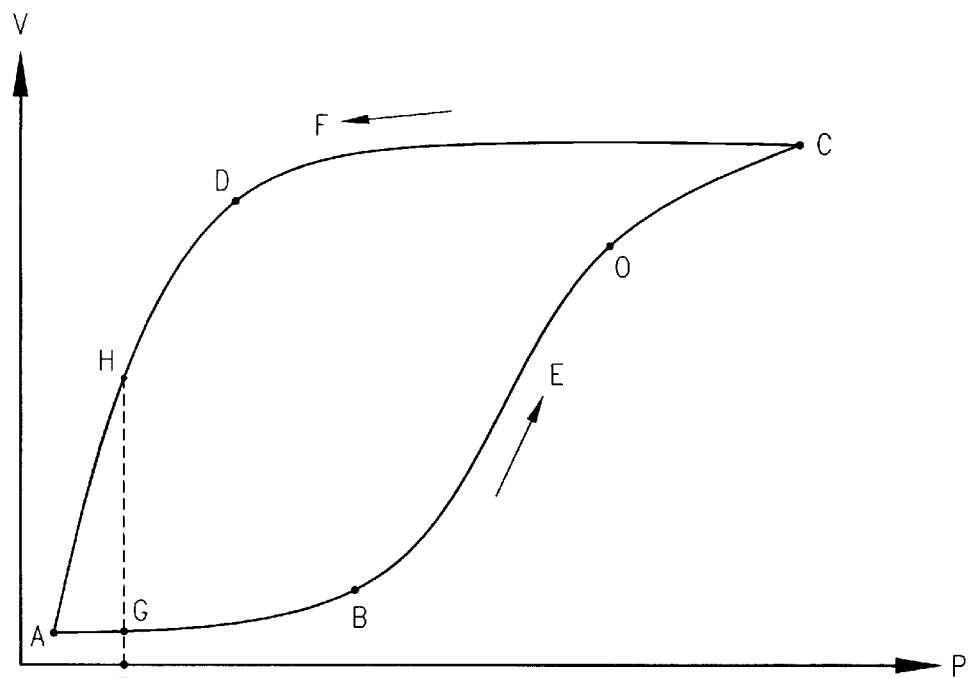
FIG. 1 is a graphic representation of the relationship between pressure and volume in the lung.

FIG. 1 shows the pressure/volume relationship of the lungs. The filling of the lungs can be caused by the negative pressure generated by the expansion of the chest wall, by a negative pressure applied to the chest by a mechanical device, or, during ventilation, by a positive pressure applied through the airway opening to the lungs. During ventilation, the lungs empty as the positive pressure applied through the airway opening to the lungs decreases.

The lungs possess elasticity, referred to as compliance. Further, the body cavity exerts resistive forces. Consequently, the rate of filling and the rate of emptying the lungs is only linear for a portion of the breathing process. Additionally, the rate of filling the lungs is not the same as the rate of emptying the lungs. These different rates result in a hysteresis effect in the breathing process, as shown in FIG. 1.

Filling of the lungs begins at point A, and follows the curve E in a counter-clockwise direction. An important location on the pressure/volume curve is point B, the point at which lung volume begins to increase at a significant rate. The curve is substantially linear between point A and point B. Point B is referred to as the lower inflection point, and the pressure corresponding to this point is known as the critical opening pressure. After the critical opening pressure has been reached in a patient receiving artificial ventilation, a majority of the air sacs which are capable of recruitment are recruited, with a concomitant increase in the gas exchange capabilities of the patient's lungs. Consequently, it is desirable to inflate the lungs with PEEP or Paw above the critical opening pressure, in order to maximize recruitment.

Inspiration continues as lung pressure increases. The curve is substantially linear between point B and point O. Point O is the upper inflection point, referred to as the point of overdistention pressure. The pressure corresponding to this point is the pressure at which overinflation begins to occur. After the overdistention point has been reached, the lung can be damaged by overinflation. Consequently, it is desirable to inflate the lungs with peak inspiratory pressures or Paw lower than the overdistenstion pressure.

Inspiration continues along the curve as lung pressure increases until, at the highest pressure applied at point C, the lungs are at their highest volume as determined by their compliance. The lower portion of the curve between point A and point C is referred to as the inspiratory limb.

The emptying of the lungs continues in a counter-clockwise direction along the curve. Another important point on the pressure/volume curve is point D, the point at which the lung begins to rapidly collapse. The curve is substantially linear between point C and point D. Point D is referred to as the pressure corresponding to the point known as the critical closing pressure. After the critical closing point has been reached in a patient receiving artificial ventilation, a majority of the patient's diseased or otherwise unhealthy air sacs are likely to derecruit, reducing the gas exchange capability of the lungs and placing the patient at risk for atelectasis. Consequently, after the lung has been inflated, it is desirable to maintain PEEP or Paw above the critical closing point.

Expiration continues as lung pressure decreases until, at the lowest pressure applied at point A, the lungs are at their lowest volume. The upper portion of the curve between point C and point A is referred to as the expiratory limb.

Because of the hysteresis effect discussed above, at any pressure F, the lung volume H is higher on the expiratory limb of the curve than the lung volume G on the inspiratory limb of the curve.

RIP is a non-invasive lung volume measuring technique that is known in the art. RIP utilizes two elastic cloth bands containing insulated wires, which encircle the patient's rib cage and abdomen. The wires within each band are connected to an oscillator module that creates a waveform of a given voltage and frequency, transmitting that waveform through the insulated wires contained within the elastic cloth bands. Respiratory movements produce variations in the self-inductance of the wire, thereby changing the frequency of the waveform. The frequency is demodulated to produce analog waveforms of chest and abdomen distensions. The voltage from the RIP increases linearly as a function of the cross-sectional area of the wires. When calibrated against a known volume, the separate measurements of chest and abdomen movement can be summed to indicate a change in lung volume. This is known in the art as an accurate method for measuring tidal volume, which is the amount of air inspired and expired by the patient.

Figure 2:
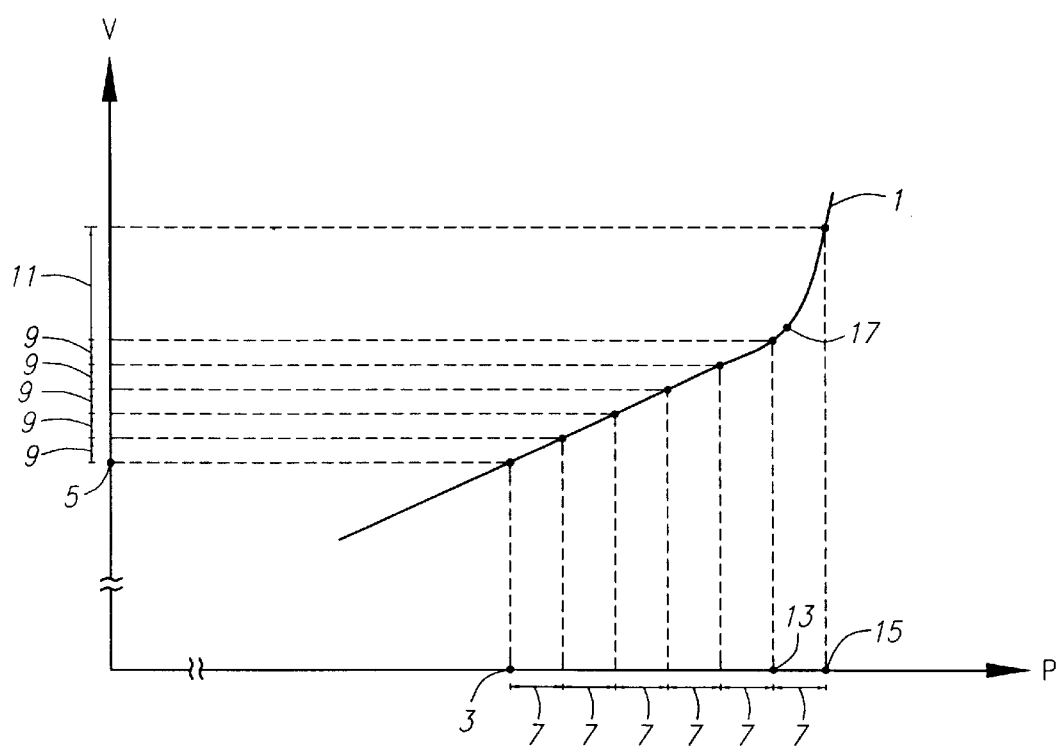
FIG. 2 is a graphic representation of a portion of the relationship between inspiration pressure and volume in the lung near the critical opening pressure, showing how respiratory inductive plethysmography (RIP) is used to determine the critical opening pressure.

Turning now to FIG. 2, a portion of the inspiratory limb 1 of the lung pressure/volume relationship near the critical opening pressure 17 is shown. To determine the critical opening pressure 17, an initial pressure 3 is applied to the patient's lungs through the airway. This initial pressure 3 is set at a level below which the critical opening pressure 17 is expected to be found. The initial pressure 3 must be set at a lower level than the critical opening pressure 17 due to the hysteresis effect in ventilation. In order to travel along the inspiratory limb 1, the pressure must increase with time. If pressure were to decrease with time, the patient's lungs would travel along the expiratory limb of the pressure/volume relationship.

At the initial pressure 3, a lung volume 5 is measured. Preferably, lung volume is measured with a SensorMedics RESPITRACE PLUS (TM) RIP device. However, any other measuring technique or device that provides accurate lung volume measurements can be used, including strain gauges, imaging techniques, transducers mounted in or on the chest wall, or volume recording jackets.

Next, the pressure applied to the patient's lungs through the airway is increased by a fixed increment 7. Preferably, this pressure increase is controlled electronically by a computing device to ensure accuracy. However, a manual pressure increase may be used if the operator can accurately control the increase. The fixed increment 7 of pressure increase creates a volume increase 9.

The pressure is then increased in a series of fixed increments 7. After each increase in pressure, the resulting lung volume is measured. The inspiratory limb 1 is substantially linear at lower pressures than the critical opening pressure 17. However, it is not completely linear. Further, as with all measurements, some error will affect lung volume measurements. Consequently, each fixed increment 7 of pressure increase to the left of the critical opening pressure 17 will not result in an equal volume increase 9. Rather, each volume increase 9 is within ±20% of the previous volume increase 9 along the substantially linear portion of the curve.

At the critical opening pressure 17, lung volume begins to increase at a significant rate, and the inspiratory limb 1 ceases to be linear. Consequently, after the last pre-critical pressure 13, the pressure increase by the fixed increment 7 creates a volume increase 11 which is >20% of the previous volume increase 9. This large volume increase 11 alerts the computing device or the operator that the critical opening pressure has been passed, and is located between the last pre-critical pressure 13 and the first post-critical pressure 15. Clinically, the caregiver will want to maintain the lung pressure above the critical opening pressure 17 to prevent atelectasis.

Figure 3:
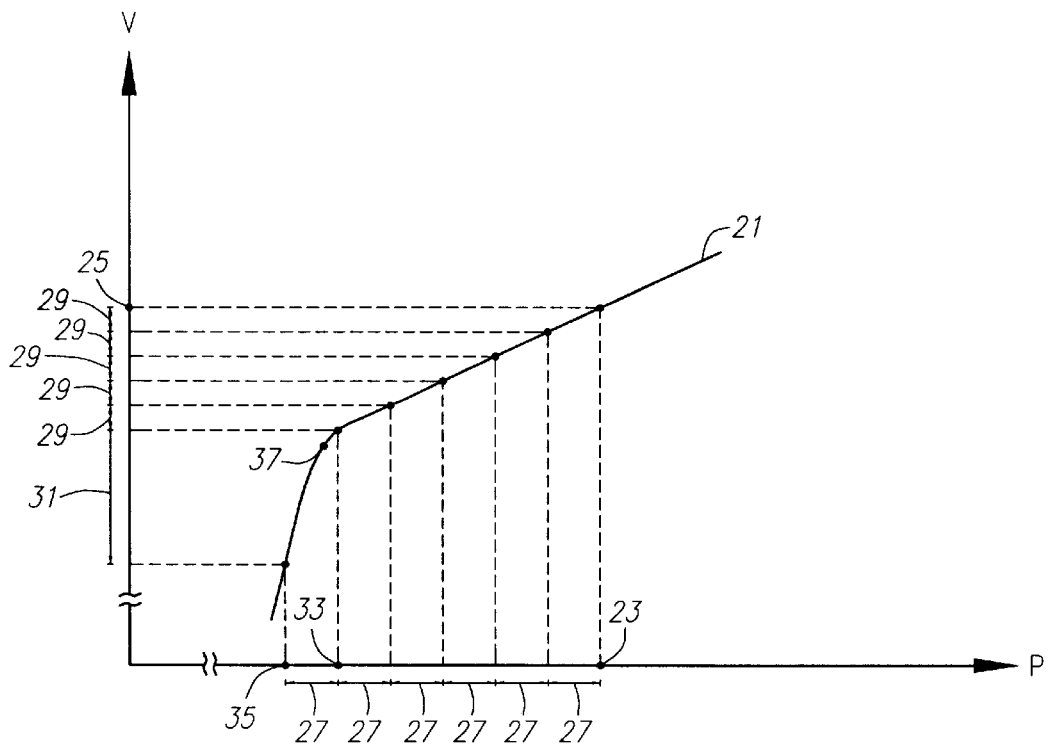
FIG. 3 is a graphic representation of a portion of the relationship between expiration pressure and volume in the lung near the critical closing pressure, showing how RIP is used to determine the critical closing pressure.

The caregiver must also ensure that the lung pressure is adequate to prevent derecruitment on the expiratory limb. Turning to FIG. 3, a portion of the expiratory limb 21 of the lung pressure/volume relationship near the critical closing pressure 37 is shown. The determination of the critical closing pressure 37 on the expiratory limb 21 is similar to the determination of the critical opening pressure 17 on the inspiratory limb 1. To determine the critical closing pressure 37, an initial pressure 23 is applied to the patient's lungs through the airway. This initial pressure 23 is set at a level above which the critical closing pressure 37 is expected to be found. The initial pressure 23 must be set at a higher level than the critical closing pressure 37 due to the hysteresis effect in ventilation. In order to travel along the expiratory limb 21, the pressure must decrease with time. If pressure were to increase with time, the patient's lungs would be traveling along the inspiratory limb of the pressure/volume relationship.

At the initial pressure 23, a lung volume 25 is measured. Preferably, lung volume is measured with a SensorMedics RESPITRACE PLUS (TM) RIP device. However, any other measuring technique or device that provides accurate lung volume measurements can be used, including strain gauges, imaging techniques, transducers mounted in or on the chest wall, or volume recording jackets.

Next, the pressure applied to the patient's lungs through the airway is decreased by a fixed increment 27. Preferably, this pressure increase is controlled electronically by a computing device to ensure accuracy. However, a manual pressure increase may be used if the operator can accurately control the increase. The fixed increment 27 of pressure decrease creates a volume decrease 29.

The pressure is then decreased in a series of fixed increments 27. After each decrease in pressure, the resulting lung volume is measured. The expiratory limb 21 is substantially linear at higher pressures than the critical closing pressure 37. However, it is not completely linear. Further, as with all measurements, some error will affect lung volume measurements. Consequently, each fixed increment 27 of pressure decrease to the right of the critical closing pressure 37 will not result in an equal volume decrease 29. Rather, each volume decrease 29 is within ±20%. of the previous volume decrease 9 along the substantially linear portion of the curve.

At the critical closing pressure 37, lung volume begins to decrease at a significant rate, and the expiratory limb 21 ceases to be linear. Consequently, after the last pre-critical pressure 33, the pressure decrease by the fixed increment 27 creates a volume decrease 31 which is >20% of the previous volume decrease 29. This large volume decrease 31 alerts the computing device or the operator that the critical closing pressure has been passed, and is located between the last pre-critical pressure 33 and the first post-critical pressure 35. Clinically, the caregiver will want to maintain the lung pressure above the critical closing pressure 17 to prevent derecruitment.

Figure 4:
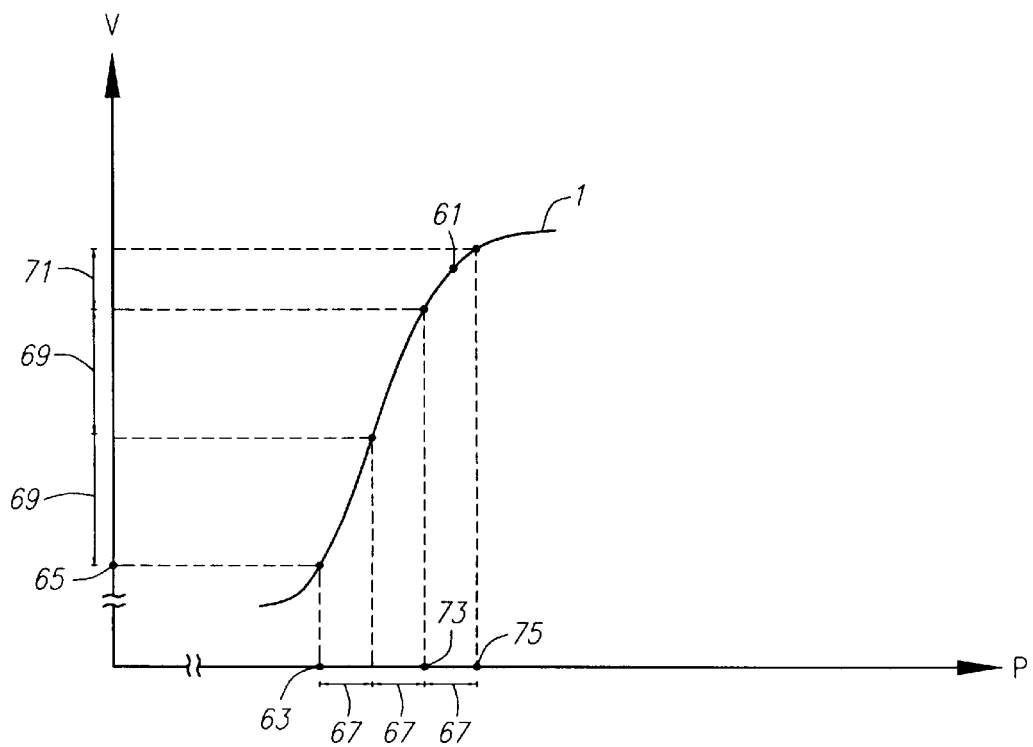
FIG. 4 is a graphic representation of a portion of the relationship between inspiration pressure and volume in the lung near the overdistension pressure, showing how RIP is used to determine the overdistention pressure when HFV is used.

The caregiver can determine the overdistention pressure corresponding to the upper inflection point with a similar method. Turning now to FIG. 4, a portion of the inspiratory limb 1 of the lung pressure/volume relationship near the overdistension pressure 61 is shown. The determination of the overdistension pressure 61 on the inspiratory limb 1 is similar to the determination of the critical opening pressure 17 on the inspiratory limb 1. To determine the overdistention pressure 61, an initial pressure 63 is applied to the patient's lungs through the airway. This initial pressure 63 is set at a level below which the overdistension pressure 61 is expected to be found. The initial pressure 63 must be set at a lower level than the critical opening pressure 17 due to the hysteresis effect in ventilation. In order to travel along the inspiratory limb 1, the pressure must increase with time. If pressure were to decrease with time, the patient's lungs would be traveling along the expiratory limb of the pressure/volume relationship and the upper inflection point could not be found.

At the initial pressure 63, a lung volume 65 is measured. Preferably, lung volume is measured with a SensorMedics RESPITRACE PLUS (TM) RIP device. However, any other measuring technique or device that provides accurate lung volume measurements can be used, including strain gauges, imaging techniques, transducers mounted in or on the chest wall, or volume recording jackets.

Next, the pressure applied to the patient's lungs through the airway is increased by a fixed increment 67. Preferably, this pressure increase is controlled electronically by a computing device to ensure accuracy. However, a manual pressure increase may be used if the operator can accurately control the increase. The fixed increment 67 of pressure increase creates a volume increase 69.

The pressure is then increased in a series of fixed increments 67. After each increase in pressure, the resulting lung volume is measured. The inspiratory limb 1 is substantially linear at higher pressures than the critical opening pressure 17. However, it is not completely linear. Further, as with all measurements, some error will affect lung volume measurements. Consequently, each fixed increment 67 of pressure increase to the right of the critical opening pressure 17 will not result in an equal volume increase 69. Rather, each volume increase 69 is within ±20% of the previous volume increase 9 along the substantially linear portion of the curve.

At the overdistention pressure 61, lung volume begins to increase at a significantly slower rate, and the inspiratory limb 1 ceases to be linear. Consequently, after the last pre-overdistention pressure 73, the pressure increase by the fixed increment 67 creates a volume increase 71 which is >20% less than the previous volume increase 69. This lesser volume increase 71 alerts the computing device or the operator that the overdistention pressure has been passed, and is located between the last pre-overdistention pressure 73 and the first post-overdistention pressure 75. Clinically, the caregiver will want to maintain the lung pressure below the overdistention pressure 61 to prevent lung damage and other serious harm to the patient.

Figure 5:
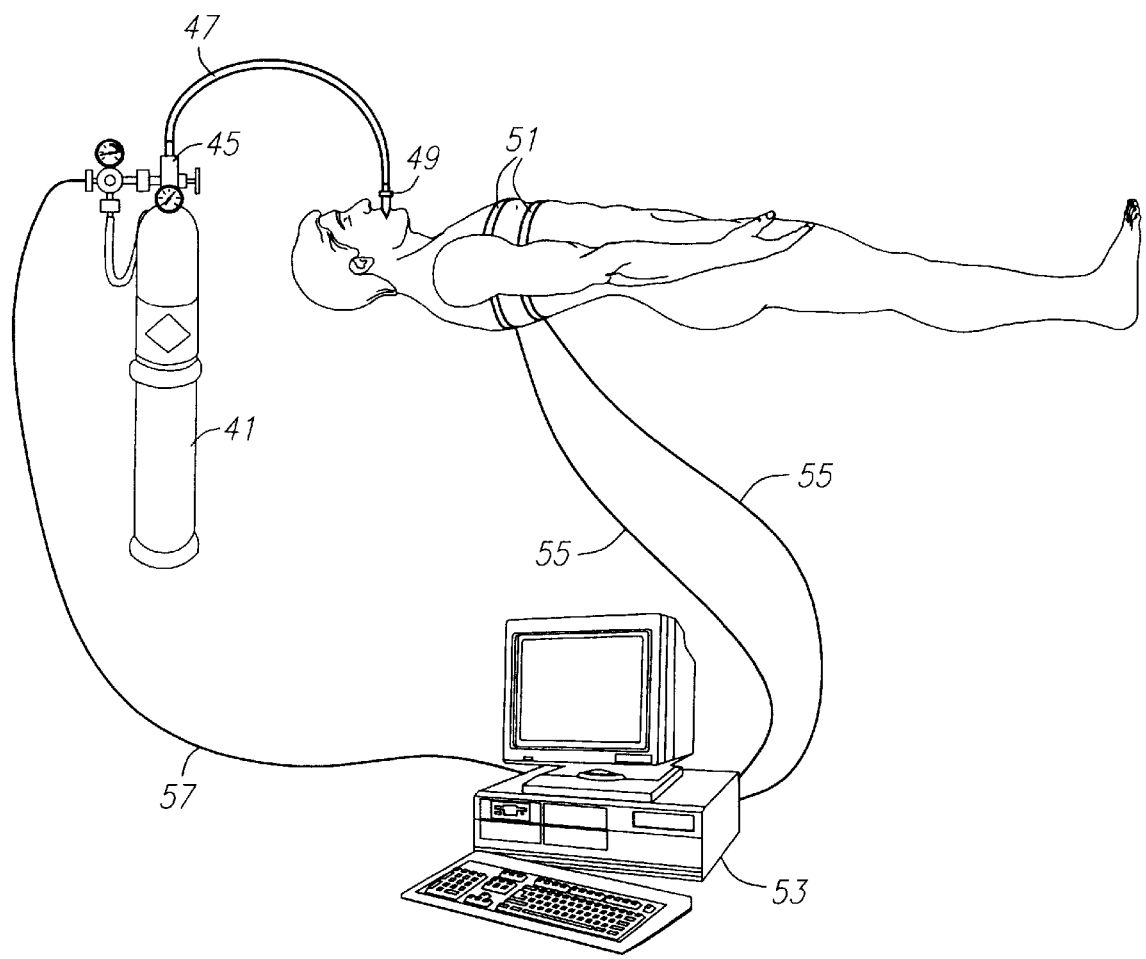
FIG. 5 is a schematic view of a ventilation pressure optimizer apparatus.

The preferred embodiment of an apparatus is shown in FIG. 5. A gas supply 41 provides ventilation gas to a patient. The gas supply 41 is preferably a cylinder of compressed air, but other sources or types of gases capable of sustaining a patient on artificial ventilation may be used. A regulator 45 controls the pressure of the gas exiting the gas supply 41.

The regulator 45 is electronically controlled, preferably by digital signals; however, analog signals may be used as well. Gas travels from the gas supply 41 to the patient through a hose 47, which ends at an endpiece 49. The endpiece 49 may take the form of a mouthpiece or of a tracheal tube adapter, depending on the treatment needs of the patient as determined by the caregiver.

As gas enters the patient at a pressure set by the regulator 45, a lung volume measurement device 51 measures the volume corresponding to that pressure and outputs that volume as electronic signals, preferably digital. Preferably, the lung volume measuring device 51 is a SensorMedics RESPITRACE PLUS (TM) RIP device. However, any other measuring technique or device that provides accurate lung volume measurements can be used, including strain gauges, imaging techniques, transducers mounted in or on the chest wall, or volume recording jackets.

A computing device 53 receives data from the lung volume measuring device 51 through wires 55. The computing device 53 transmits a signal to the regulator 45 through wire 57 to allow gas from the gas supply 41 to reach the patient at an initial pressure. The computing device 53 then receives electronic signals from the lung volume measuring device 51, transmitting a lung volume measurement. The computing device 53 correlates that lung volume measurement with the pressure at which the computing device has set the regulator 45. Next, the computing device 53 transmits a signal to the regulator 45 to increase the pressure to the patient by a substantially fixed increment. Again, the computing device 53 receives a volume measurement from the lung volume measuring device 51 and correlates that volume measurement with the pressure at which the computing device has set the regulator 45. The computing device 53 continues to increase the pressure to the patient by substantially equal increments, receiving a volume measurement from the lung volume measuring device 51 after each increment. In this way, the computing device 53 determines the critical opening pressure of the lungs, following the method hereinbefore disclosed. Advantageously, the computing device 53 may be programmed to cease increasing the pressure to the patient after it has determined the critical opening pressure.

In a similar manner, the apparatus determines the critical closing pressure of the lungs by establishing an initial pressure to the patient, then utilizing the computing device 53 to decrease the pressure to the patient by fixed increments. After each increment, the lung volume measuring device 51 transmits a volume measurement to the computing device. In this way, the computing device determines the critical closing pressure of the lungs, following the method hereinbefore disclosed. Advantageously, the computing device 53 may be programmed to cease decreasing the pressure to the patient after it has determined the critical closing pressure.

A preferred ventilator pressure optimization method and apparatus and many of its attendant advantages have thus been disclosed. It will be apparent, however, that various changes may be made in the form, construction, and arrangement of the parts without departing from the spirit and scope of the invention, the form hereinbefore described being merely a preferred or exemplary embodiment thereof. Therefore, the invention is not to be restricted or limited except in accordance with the following claims.

What is claimed is:

1. A method for determining the critical opening pressure of the lungs, comprising the steps of:
    (a) applying a known pressure lower than the critical opening pressure to the lungs of a patient through his or her airway;
    (b) increasing the pressure applied to the lungs in substantially equal stepwise pressure increments;
    (c) measuring the approximate lung volume at each of the stepwise pressure increments;
    (d) determining the approximate lung volume increase resulting from the present stepwise pressure increment;
    (e) stopping when the lung volume increase resulting from the present stepwise pressure increment differs from the lung volume increase resulting from the previous stepwise pressure increment by more than 20%; and
    (f) displaying the final pressure.

2. The method of claim 1, further comprising a step of electronically transmitting the final pressure to a ventilator.

3. A method for determining the critical closing pressure of the lungs, comprising the steps of:
    (a) applying a known pressure greater than the critical closing pressure to the lungs of a patient through his or her airway;
    (b) decreasing the pressure applied to the lungs in substantially equal stepwise pressure decrements;
    (c) measuring the approximate lung volume at each of the stepwise pressure decrements;
    (d) determining the approximate lung volume decrease resulting from the present stepwise pressure decrement;
    (e) stopping when the lung volume decrease resulting from the present stepwise pressure decrement differs from the lung volume decrease resulting from the previous stepwise pressure decrement by more than 20%; and
    (f) displaying the final pressure.

4. The method of claim 3, further comprising a step of electronically transmitting the final pressure to a ventilator.

5. A method for determining the overdistention pressure of the lungs, comprising the steps of:
    (a) applying a known pressure lower than the overdistention pressure to the lungs of a patient through his or her airway;
    (b) increasing the pressure applied to the lungs in substantially equal stepwise pressure increments;
    (c) measuring the approximate lung volume at each of the stepwise pressure increments;
    (d) determining the approximate lung volume increase resulting from the present stepwise pressure increment;
    (e) stopping when the lung volume increase resulting from the present stepwise pressure increment differs from the lung volume increase resulting from the previous stepwise pressure increment by less than 20%; and
    (f) displaying the final pressure.

6. The method of claim 5, further comprising a step of electronically transmitting the final pressure to a ventilator.

7. A method for determining the critical opening pressure of the lungs, comprising the steps of:
    (a) applying a known pressure lower than the critical opening pressure to the lungs of a patient;
    (b) measuring the approximate lung volume resulting from that pressure;
    (c) increasing the pressure to the lungs of a patient by a known increment;
    (d) measuring the lung volume resulting from the known increment of pressure;
    (e) determining the approximate difference between lung volume measured before the incremental increase in pressure and lung volume after the incremental increase in pressure;

(f) repeating steps (d) and (e);
(g) comparing said differences calculated in steps (e) and (f), stopping when said difference calculated in step (f) differs from the difference calculated in step (e) by more than 20%.

8. A method for determining the critical closing pressure for lung ventilation, comprising the steps of:
   (a) applying a known pressure greater than the critical closing pressuer to the lungs of a patient;
   (b) measuring the approximate lung volume resulting from that pressure;
   (c) decreasing the pressure to the lungs of a patient by a known decrement;
   (d) measuring the lung volume resulting from the known decrement of pressure;
   (e) determining the approximate difference between lung volume measured before the decremental decrease in pressure and lung volume after the decremental decrease in pressure;
   (f) repeating steps (d) and (e);
   (g) comparing the differences calculated in steps (e) and (f), stopping when the difference calculated in step (f) differs from the difference calculated in step (e) by more than 20%.

9. A method for determining the overdistention pressure for lung ventilation, comprising the steps of:
   (a) applying a known pressure lower than the overdistention pressure to the lungs of a patient;
   (b) measuring the approximate lung volume resulting from that pressure;
   (c) increasing the pressure to the lungs of a patient by a known increment;
   (d) measuring the lung volume resulting from the known increment of pressure;
   (e) determining the approximate difference between lung volume measured before the incremental increase in pressure and lung volume after the incremental increase in pressure;
   (f) repeating steps (d) and (e);
   (g) comparing the differences calculated in steps (e) and (f), stopping when the difference calculated in step (f) differs from the difference calculated in step (e) by less than 20%.

10. A ventilation pressure optimization apparatus, comprising:
    (a) a gas supply;
    (b) a pressure regulator for varying in substantially equal increments the pressure delivered by the gas supply to a patient;
    (c) a lung volume measurement device; and
    (d) a computing device connected to said pressure regulator and to said lung volume measuring device; the computing device controlling the pressure to the patient by incrementally changing the pressure delivered through the pressure regulator to the patient in substantially equal increments, correlating the pressure of each increment with the resulting measurement from the lung volume measuring device, and stopping when the lung volume change between the current pressure increment and the last pressure increment differs from the lung volume change between the last pressure increment and the pressure increment preceding it by a preset amount.

11. The ventilation pressure optimization apparatus of claim 10, wherein said lung volume measurement device is an RIP device.

12. The ventilation pressure optimization apparatus of claim 10, further comprising a display for displaying lung volume measurements and pressure regulator control pressures.

13. The ventilation pressure optimization apparatus of claim 10, wherein said gas supply is a cylinder of atmospheric gas.

* * * * *